United States Patent [19]

Brachwitz et al.

[11] Patent Number: 4,916,249
[45] Date of Patent: Apr. 10, 1990

[54] GLYCERO-3(2)-PHOSPHO-L-SERINE DERIVATIVES AND SALTS THEREOF

[76] Inventors: Hans Brachwitz; Peter Langen; Christine Lehmann; Eckart Matthes; Jurgen Schildt; Iduna Fichtner, all of c/o Academy of Sciences, Otto-Nuschke-Strasse 22/23, D-x 1086 Berlin, German Democratic Rep.; Albin Hermetter; Friedrich Paltauf, both of c/o Technical University of Graz, Schlogelgasse 9, A-8010 Graz, Austria

[21] Appl. No.: 376,161

[22] Filed: Jul. 7, 1989

Related U.S. Application Data

[63] Continuation of Ser. No. 19,277, filed as PCT EP86/00390 on Jul. 2, 1986, published as WO87/00173 on Jan. 15, 1987, abandoned.

[30] Foreign Application Priority Data

| Jul. 3, 1985 [DD] | German Democratic Rep. ............... 2782300 |
| Jul. 3, 1985 [DD] | German Democratic Rep. ............... 27823170 |
| Jul. 15, 1985 [DD] | German Democratic Rep. ............... 2785600 |
| Jul. 15, 1985 [DD] | German Democratic Rep. ............... 2785625 |

[51] Int. Cl.$^4$ ............... C07F 9/10
[52] U.S. Cl. ............... 558/169
[58] Field of Search ............... 558/169

[56] References Cited

U.S. PATENT DOCUMENTS

| 3,264,378 | 8/1966 | Dailey et al. ............ 558/169 |
| 3,632,627 | 1/1972 | Gordon et al. ........... 558/169 |
| 4,372,949 | 2/1983 | Kodama et al. .......... 558/169 |

FOREIGN PATENT DOCUMENTS

| 155168 | 5/1982 | German Democratic Rep. ............ 558/169 |
| 239208 | 9/1986 | German Democratic Rep. ............ 558/169 |
| 239209 | 9/1986 | German Democratic Rep. ............ 558/169 |

*Primary Examiner*—Anton H. Sutto
*Attorney, Agent, or Firm*—Wenderoth, Lind & Ponack

[57] ABSTRACT

The invention relates to novel glycero-3(2)phospho-L-serine derivatives of the general formula

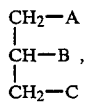

I in which A represents unsubstituted or substituted (C5-C30) alkoxy, or unsubstituted or substituted (C5-C30) alkenoxy, whereby a double bond of the alkenoxy residue does not originate at the C atom bound to oxygen, or halogen, or a group of the general formula

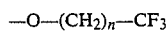

II, wherein n is 0 or an integer 1, 2 or 3, one of the two residues B and C, which is identical to or different from A, has one of the definitions given for A or represents hydrogen, and the respective other residue represents the phosphatidyl-L-serine group of the formula

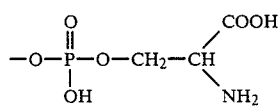

III with the proviso that at least one residue A, B or C represents (C5-C30) alkoxy or (C5-C30) alkenoxy; and the pharmaceutically acceptable salts of compounds of general formula I with bases, a process for the preparation thereof, pharmaceutical preparations containing the said compounds, and their use in drugs with cytostatic activity.

1 Claim, No Drawings

GLYCERO-3(2)-PHOSPHO-L-SERINE DERIVATIVES AND SALTS THEREOF

This application is a continuation of application Ser. No. 19,277, filed as PCT EP86/00390 on Jul. 2, 1986, published as WO87/00173 on Jan. 15, 1987, now abandoned.

The invention relates to novel glycero-3(2)-phospho-L-serine derivatives of the general formula

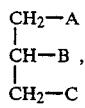   I in which A represents unsubstituted or substituted (C5-C30) alkoxy, or unsubstituted or substituted (C5-C30) alkenoxy, whereby a double bond of the alkenoxy residue does not originate at the C atom bound to oxygen, or halogen, or a group of the general formula

   II, wherein n is 0 or an integer 1, 2 or 3, one of the two residues B and C, which is identical to or different from A, has one of the definitions given for A or represents hydrogen, and the respective other residue represents the phosphatidyl-L-serine group of the formula

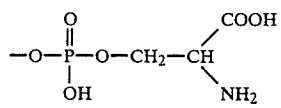   III with the proviso that at least one residue A, B or C represents (C5-C30) alkoxy or (C5-C30) alkenoxy; and the pharmaceutically acceptable salts of compounds of general formula I with bases, a process for the preparation thereof, pharmaceutical preparations containing the said compounds, and their use in drugs with cytostatic activity.

The glycerophospho-L-serine derivatives of general formula I in each case have a chirality center in the serine portion of the molecule and can possess a second chirality center in the glycerin portion of the molecule as a function of the definition of residues A, B, and C. Consequently, the object of the invention and covered by the general formula I are likewise all possible chiral and diastereomeric forms of the novel compounds.

The term "alkoxy" employed in this description relates to straight-chain, singly or repeatedly branched alkyl ether groups, which preferably have 14-20 carbon atoms and especially preferably 16-18 carbon atoms. Examples of preferred alkoxy residues are tetra-, penta-, hexa-, hepta-, octa-, nonadecyloxy, eicosyloxy, or the branched analogs thereof. The term "alkenyloxy" stands for straight-chain, singly or repeatedly branched, singly or repeatedly unsaturated alkenyl ether groups, which preferably have 14-20 and especially preferably 16-18 carbon atoms, whereby in these alkenyl ether groups, enol ether groups in which an olefinic double bond originates at the carbon atom bound to oxygen are explicitly excluded. Both the alkoxy residues and alkenoxy residues A, B, and C, more closely described above, can be substituted once or repeatedly, preferably once, whereby possible substituents are preferably halogen, hydroxy, alkoxy, or cyano.

The term "halogen" refers to the four halogens, chlorine, bromine, iodine, and fluorine, whereby chlorine and fluorine are especially preferred.

In a preferred class of compounds of general formula I, C represents the phosphatidyl-L-serine group of formula III, one of the residues A and B, alkoxy or alkenoxy, and the respective other residue, halogen.

Another preferred class relates to compounds of general formula I, wherein C represents the phosphatidyl-L-serine group of formula III, one of the residues A and B, alkoxy or alkenoxy, and the respective other residue, a terminally fluorinated alkoxy residue of formula II.

Also preferred are such compounds of general formula I, wherein A represents alkoxy or alkenoxy, B, hydrogen or alkoxy, and C, the phosphatidyl-L-serine group of formula III.

Finally, also preferred is that class of compounds of general formula I, wherein B represents the phosphatidyl-L-serine group of formula III, one of the residues A and C, alkoxy or alkenoxy, and the respective other residue, halogen.

Especially preferred individual compounds of the invention are:
1-O-hexadecyl-2-chloro-2-deoxyglycero-3-phospho-L-serine,
1-O-hexadecyl-2-fluoro-2-deoxyglycero-3-phospho-L-serine,
1-chloro-1-deoxy-3-O-hexadecylglycero-2-phospho-L-serine,
1-chloro-1-deoxy-2-O-hexadecylglycero-3-phospho-L-serine,
1-O-hexadecyl-2-deoxyglycero-3-phospho-L-serine,
1,2-di-O-hexadecylglycero-3-phospho-L-serine,
1-O-(2,2,2-trifluoroethyl)-2-O-hexadecylglycero-3-phospho-L-serine,
1-O-hexadecyl-2-O-(2,2,2-trifluoroethyl)-glycero-3-phospho-L-serine,
1-chloro-1-deoxy-2-O-octadecylglycero-3-phospho-L-serine,
1-O-octadecyl-2-(2,2,2-trifluoroethyl)-glycero-3-phospho-L-serine,
1-O-octadecyl-2-chloro-2-deoxyglycero-3-phospho-L-serine.

The glycero-3(2)-phospho-L-serine derivatives of general formula I and the pharmaceutically acceptable salts thereof are prepared according to the invention by methods known per se, preferably in so doing (a) a glycero-3(2)-phosphoric acid derivative of the general formula

   IV in which A is defined as in formula I, one of the two residues D and E has one of the definitions given in formula I for A or is hydrogen, and the respective other residue represents a group of the general formula

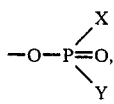   V wherein X and Y are either identical and represent hydroxy or halogen or Y is a lower alkoxy or aryloxy, with the proviso that at least one residue A, D or E represents (C5-C30) alkoxy or (C5-C30) alkenoxy, or the salts thereof with a protected L-serine derivative of the general formula

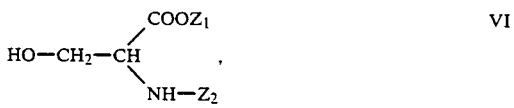

in which Z1 represents a carboxyl and Z2 an amino protective group, is reacted preferably in the presence of a condensation agent, then the protective groups Z1 and Z2 are removed, in any order or concurrently, and if necessary the resulting glycerophosphoric acid esters or halides are saponified, or (b) a glycero-3(2)-phosphoric acid ester of the general formula

in which A is defined as in formula I, one of the two residues L and M has one of the definitions given for A in formula I or is hydrogen, and the respective other residue represents a group of the general formula

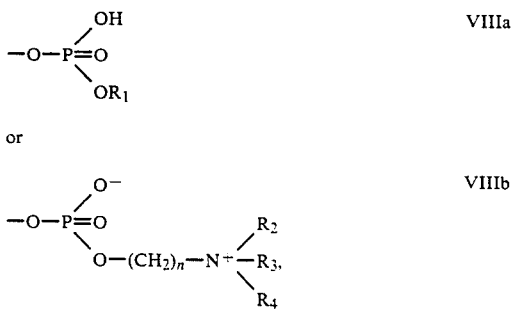

wherein R1 represents a (C1-C6) alkyl substituted by hydroxy or halogen if necessary, R2, R3, and R4, which are identical or different, independently represent hydrogen or methyl, and n an integer from 1 to 6, with the proviso that at least one residue A, L or M represents (C5-C30) alkoxy or (C5-C30) alkenoxy, is reacted with L-serine in the presence of phospholipase D, and the resulting compounds of general formula I or salts thereof are isolated, and (c) if so desired a compound of general formula I obtained by process variant (a) or (b) or a pharmaceutically unacceptable salt thereof is converted into a pharmaceutically acceptable salt.

According to process variant (a), the compounds of general formula I can be prepared from glycero-3(2)-phosphoric acid derivatives of formula IV and appropriately protected L-serines of formula VI by methods familiar to the artisan and known per se. For example, it is known that phosphatidylserines with saturated and unsaturated acyl residues can be prepared by condensation of phosphatidic acids with serines with protected amino and carboxyl groups or by reaction of diacylglycerol iodohydrines with protected O-phosphoserines, whereby the protective groups of the protected phosphatidylserine forming as an intermediate can be cleaved concurrently or sequentially by suitable methods. Phosphatidic acid chlorides were also used in the reaction instead of phosphatidic acids. Alkyl- and alkylene-substituted glycerophosphoserines can also be synthesized in a similar way (A. J. Slotboom and P. P. Bonsen, Chem. Phys. Lipids 5, (1970), 301–398; M. Kates, in: E. D. Korn (editor), Methods in Membrane Biology, Vol. 8, Plenum Press, New York, 1977, p. 119ff; H. Eibl, Chem. Phys. Lipids 26, (1980), 405–429; A. Hermetter, F. Paltauf, and H. Hauser, Chem. Phys. Lipids 30, (1982), 35–45).

Appropriately substituted glycero-3(2)-phosphoric acids of formula IV, in which one residue D or E represents a group of formula V, wherein X and Y are hydroxy, are preferred for the preparation of the novel glycero-3(2)-phospho-L-serine derivatives of general formula I.

The corresponding phosphoric acid dihalides (X and Y in V: halogen), preferably phosphoric acid dichlorides, which are obtained by reacting the appropriately substituted glycerols with phosphorus oxyhalides, can also be used instead of the free acids. When these phosphoric acid dihalides of formula IV (X and Y in V: halogen) are reacted with a protected type VI serine, the resulting intermediates are glycerophospho-L-serine chlorides, with a protected serine group, of compounds of general formula I, which can be converted into compounds of general formula I or salts thereof before or after their isolation and before, during or after the removal of the protective groups.

Another variant of the novel process is that the protected serines of formula VI are reacted with glycerophosphoric acid ester halides of formula IV, in which one residue D or E is such a group of formula V, wherein X represents halogen, preferably chlorine, and Y a lower alkoxy or aryloxy. The alkyl or aryl esters, obtained as intermediates and protected at the serine group, of compounds of general formula I can be converted according to conventional chemical methods by hydrolysis and cleavage of protective groups into the acids of general formula I or salts thereof.

Glycerophosphoric acid alkyl(-aryl) ester halides of formula IV are readily available by reacting the appropriately substituted glycerols with phosphoric acid alkyl (or aryl) ester dihalides.

Suitable as protected L-serine derivatives for use in the novel reaction are such compounds of formula VI, wherein Z1 represents a carboxyl protective group such as benzyl, tert-butyl, phthalimidomethyloxy, isopropyl, benzhydryl or the like, which is used in peptide chemistry and is readily cleavable, for example, by catalytic hydrogenolysis, hydrazinolysis, treatment with HCl or sodium thiophenolate, or by hydrolysis, and Z2 an amino protective group, which is typically used in peptide chemistry and removable, for example, by catalytic hydrogenolysis, hydrazinolysis, or treatment with HCl or formic acid. Such amino protective groups are, for example, acyl groups, such as formyl, acetyl, trifluoroacetyl; alkoxy carbonyl groups, such as ethoxycarbonyl, tert-butoxycarbonyl, beta,beta,beta-trichloroethoxycarbonyl, beta-iodoethoxycarbonyl; aralkoxycarbonyl such as benzyloxycarbonyl, p-methoxybenzyloxycarbonyl; aryloxycarbonyl such as phenoxycarbonyl; silyl groups such as trimethylsilyl; and other groups such as trityl, tetrahydropyranyl, vinyloxycarbonyl, O-nitrophenylsulfenyl, diphenylphosphinyl, p-toluenesulfonyl, benzyl, and the like.

The protective groups Z1 and Z2 can be selected as desired per se, but it is generally advantageous to select such protective group combinations to protect the L-serine, that can be cleaved in one reaction step, by, for example, using N-tert-butoxy-L-serine benzhydryl ester and the like as the protected serine derivative.

The reaction of compounds of formula IV with those of formula VI to product derivatives of compounds of general formula I, which are formed as intermediates according to process step (a) and still protected at the serine group, is generally carried out so that a glycero-3(2)-phosphoric acid derivative of formula IV, preferably a well-dried salt of a glycero-3(2)-phosphoric acid of formula IV, e.g., the pyridinium salt, is reacted with the protected serine of formula VI at a molar ratio of 1:1 to 1:5 in the presence of a strong base such as pyridine, triethylamine, Huenig's base, and the like, and if necessary of an additional inert, nonpolar organic solvent, such as chloroform, ethyl acetate, diethyl ether, diisopropyl ether, benzene, chlorobenzene, tetrahydrofuran, and the like.

The reaction is run preferably in the presence of a suitable condensation agent, e.g., 2,4,6-triisopropylbenzenesulfonyl chloride, at room temperature or at temperatures just below or above room temperature.

Cleavage of protective groups from the protected intermediates obtained in this reaction can proceed, depending on the protective groups selected, by methods available to all artisans. For example, intermediates in the form of benzhydryl esters protected by alkoxycarbonyl can be converted into compounds of formula I by treatment with HCl, preferably by introduction of HCl into solutions of the intermediates in organic solvents, with cleavage of both protective groups; possibly present trityl protective groups can be removed by hydrogenolysis, and others by hydrolysis, hydrazinolysis, and the like.

Compounds of general formula I can be obtained according to process step (b) from glycero-3(2)-phosphoric acid esters of general formula VII by enzymatically catalyzed transesterification with use of phospholipase D by methods known per se.

Some phospholipids have already been prepared with the use of phospholipase D (H. Eibl et al., Methods in Enzymology, 72, 1981, 632–639), whereby glycerophosphoric acid alkyl esters that do not occur naturally and analogs were used in part as substrates in the reaction. Only modest yields of phosphatidylserines were obtained to date in the enzymatic synthesis of phosphatidylserines from natural phosphatidylcholines (P. Comfurius et al., Biochim. Biophys. Acta 488, 1977, 36–42), and hydrolysis with formation of phosphatidic acids was observed primarily. Others have not been used to date as natural substrates for the preparation of phosphatidylserines by transesterification by mean of phospholipase D.

The preparation of the novel glycero-3(2)-phospho-L-serine derivatives of general formula I proceeds in principle by reacting a compound of general formula VII in aqueous solution or suspension with addition of organic solvents as solubilizers, e.g., ether and/or chloroform, and a buffer, e.g., sodium acetate buffer or tris buffer, at a pH of 4.8 to 8 in the presence of a calcium salt (molarity preferably of 0.01 to 0.1 mole/liter), with L-serine in the presence of phospholipase D at temperatures between 10° and 50° C. The process is particularly advantageous in that unprotected serine can be used for the reaction.

After the completed reaction, which can be monitored for example by thin-layer chromatography, the enzyme is inactivated, advantageously by addition of 0.1M ethylenediaminetetracetic acid solution, and then the resulting glycero-3(2)-phospho-L-serine derivative of general formula I is isolated and purified by conventional procedure, e.g., with use of chromatographic techniques, such as thin-layer, column, or high-pressure liquid chromatography.

As indicated above, all possible chiral and diastereomeric forms of novel compounds of general formula I are included. Either chiral or diastereomeric end products can be obtained according to both process variant ) and process variant (b) as a function of the steric relations in the starting materials of formula IV or formula VII. If chiral starting materials or those with no chirality center are used in one of the two described process variants, chiral forms of compounds of general formula I are obtained. If, on the contrary, racemic starting materials of formula IV or formula VII are used, diastereomeric mixtures of compounds of general formula I are obtained in the novel reaction with a protected L-serine derivative of formula VI or with L-serine itself.

The compounds obtained by process variant (a) or (b) of general formula I or pharmaceutically unacceptable salts thereof can be converted into their pharmaceutically acceptable salts by process step (c) in a conventional way with inorganic or organic bases. Salt formation can be carried out, for example, by dissolving the indicated compounds of formula I in a suitable organic solvent, e.g., a lower aliphatic alcohol, adding an equivalent amount of the desired base, mixing thoroughly, and removing the solvent by distillation in vacuum after salt formation ends.

Pharmaceutically acceptable salts are, e.g., metal salts, especially alkali metal and alkaline-earth metal salts, such as sodium, potassium, magnesium, or calcium salts. Other pharmaceutically acceptable salts also include, for example, ammonium salts, which are derived from ammonia or organic amines, e.g., mono-, di-, or tri-lower (alkyl, cycloalkyl, or hydroxyalkyl) amines, lower alkylene diamines or heterocyclic bases, e.g., methylamine, diethylamine, triethylamine, dicyclohexylamine, triethanolamine, ethylenediamine, pyridine, piperidine, piperazine, morpholine, and the like.

Pharmaceutically unacceptable salts of compounds of general formula I can be converted into pharmaceutically acceptable salts by conventional ester interchange, whereby the pharmaceutically unusable cation is replaced by a pharmaceutically usable cation. As an alternative, a pharmaceutically unusable salt can also be neutralized and then the thus obtained free acid is reacted with a base, which yields a pharmaceutically acceptable salt.

The glycero-3(2)-phosphoric acid derivatives of general formula IV employed as the starting material in process variant (a) are either known or can be prepared by methods known per se (e.g., H. Brachwitz et al., Chem. Phys. Lipids 31, 1982, 33–52; A. Hermetter et al., Chem. Phys. Lipids 30, 1982, 35–45), especially according to the more specific details given in the embodiment examples.

The glycero-3(2)-phosphoric acid esters of general formula VII employed as the starting material in process variant (b) are likewise either known or can be obtained by methods known per se (East German Patent Nos. 222 594 and 222 595).

A phospholipase D suitable for the enzymatic reaction can be obtained in accordance with methods of the prior art in a simple way from white cabbage, by homogenizing the cabbage, filtering the homogenate, and centrifuging the aqueous phase for 45 minutes at 25,000 g. The clear supernatant is combined with 2 volumes of acetate. It is decanted from the resulting precipitate with use of an immersion fritted filter, and the residue is centrifuged for 20 minutes at 13,000 g and 5° C. The acetone-moistened enzyme-containing preparation is dried in vacuum over phosphorus pentoxide.

The compounds of general formula I and salts thereof are biologically highly active and in particular possess marked antitumor activity. These valuable properties can be demonstrated in vitro and in vivo by standard methods, for example, by the fact that inhibition of the proliferation of Ehrlich ascites tumor cells has been demonstrated in vitro by treatment with glycero-3(2)-phospho-L-serine derivatives of general formula I.

In this test (Table I), the novel compounds, for example,

1-O-hexadecyl-2-chloro-2-deoxyglycero-3-phospho-L-serine (compound No. 1),

1-O-hexadecyl-2-fluoro-2-deoxyglycero-3-phospho-L-serine (compound No. 2), 1-chloro-1-deoxy-3-O-hexadecylglycero-2-phospho-L-serine (compound No. 3), 1-O-(2,2,2-trifluoroethyl)-2-O-hexadecylglycero-3-phospho-L-serine (compound No. 4), produce significant cell growth inhibition in Ehrlich ascites tumor cells even at very low concentrations.

TABLE I

Inhibition of Proliferation (%) of Ehrlich Ascites Tumor Cells in Vitro by Compounds of General Formula I as a Function of Concentration

| Compound No. | Concentration ($\mu M$) | | | | | |
|---|---|---|---|---|---|---|
| | 100 | 20 | 10 | 5 | 2 | 1 |
| | % inhibition | | | | | |
| 1 | 95 | 80 | 55 | 30 | 10 | 16 |
| 2 | 95 | 82 | 51 | 18 | 13 | 10 |
| 3 | 93 | 81 | 68 | 38 | 17 | 15 |
| 4 | 100 | 74 | 36 | 10 | | |
| C | 100 | 62 | 23 | 4 | 0 | 0 |

C = comparison substance: 1-O-octadecyl-2-O-methylglycero-3-phosphocholine

The in-vitro efficacy of the novel compounds is qualitatively comparable to the cytostatically active 1-O-octadecyl-2-O-methylglycero-3-phosphocholine, which has already found clinical application in cancer therapy (P. G. Munder et al., in: Augmenting Agents in Cancer Therapy, pp. 441–458, Raven Press, New York, 1981; W. E. Berdel et al., Cancer 50, 1982, 2011, 2015). The novel compounds have the advantage over the comparison substance that significant antitumor activity occurs even at very low concentrations, so that much lower dosage u its need to be administered to achieve the same cytostatic effect. On the basis of these properties, the novel compounds offer the expectation of more advantageous application in human medicine in the treatment and prophylaxis of tumors.

Overall, the marked antitumor activity of the novel glycero-3(2)-phospho-L-serine derivatives is surprising, because it had been assumed until now (cf. D. R. Hoffman et al., Research Commun. in Chem. Pathol. Pharmacol. 44, 1984, 239–306) that the antitumor activity of alkyl phospholipid analogs is limited to compounds with a phosphocholine group.

The compounds of general formula I can find application as therapeutic agents, e.g., in the form of pharmaceutical preparations, which contain them in a mixture with a pharmaceutical, organic or inorganic inert aid and/or carrier, suitable for enteral or parenteral administration, such as, for example, pharmaceutically safe solvents, gelatin, gum arabic, lactose, starch, magnesium stearate, talc, vegetable oils, polyalkylene glycols, petrolatum, and the like.

The pharmaceutical preparations can be provided in solid form, for example, as tablets, coated tablets, suppositories, capsules, and the like, or in liquid form, for example, as solutions, suspensions, or emulsions. If necessary, they are sterilized and contain pharmaceutical aids, such as preservatives, stabilizing or emulsifying agents, salts to alter osmotic pressure, and the like.

In particular, pharmaceutical preparations can contain the novel compounds in combination with other therapeutically valuable substances. The novel compounds can be formulated with the said substances together with the above-mentioned pharmaceutical aids and/or carriers into combination preparations.

The following examples provide a more detailed description of the invention:

EXAMPLE 1

1-O-Hexadecyl-2-chloro-2-deoxyglycero-3-phospho-L-serine

1-O-Hexadecyl-2-chloro-2-deoxyglycero-3-phosphoric acid: 335 mg (1 mmol) of 1-O-hexadecyl-2-chloro-2-deoxyglycerol is dissolved in 10 ml of dry tetrahydrofuran, 0.6 ml of pyridine is added, the thus obtained solution is added dropwise to a solution of 0.35 ml (3.755 mmol) of phosphorus oxychloride in 3.5 ml of anhydrous tetrahydrofuran at 0° C. with stirring, and the mixture is stirred for another 3 hours at 0° C. Then 16 ml of a 10% sodium bicarbonate suspension is added, the mixture is stirred for 15 minutes, the pH is adjusted to 7 with dilute hydrochloric acid, and the mixture is extracted repeatedly with ether/chloroform. The extracts are evaporated in vacuum; 390 mg (92% of theoretical) of crude product is obtained, which is sufficiently pure for use in subsequent reactions.

Rf: 0.15 (silica gel 60, Merck aluminum sheet; CHCl3/CH3OH/25% NH3=50:25:6, v/v/v).

1-O-Hexadecyl-2-chloro-2-deoxyglycero-3-phospho-N-tert-butoxycarbonyl-L-serine benzhydryl ester:

225 mg (0.54 mmol) of 1-0-hexadecyl-2-chloro-2-deoxyglycero-3-phosphoric acid, 0.3 g (0.81 mmol) of N-tert-butoxycarbonyl-L-serine benzhydryl ester, and 0.657 g (2.35 mmol) of 2,4,6-triisopropylbenzenesulfonyl chloride are stirred in 13 ml of anhydrous pyridine for 36 hours at room temperature. Some drops of water are added; the mixture is evaporated in vacuum and repeatedly distilled with toluene; the residue is taken up in ether, filtered, and evaporated.

The crude product thus obtained is adsorbed on silica gel (35 g, SG 60, Merck 40–63 $\mu m$), and sequentially eluted with 50 ml of chloroform and chloroform/methanol (9:1). Fractions of 15 ml each are obtained. Fractions 6 to 12 are combined and evaporated. 161 mg (38% of theoretical) of pure product is thus obtained.

Rf: 0.72 (silica gel 60, Merck aluminum sheet; CHCl3/CH3OH/25% NH3=65:35:5, v/v/v).

1-O-Hexadecyl-2-chloro-2-deoxyglycero-3-phospho-L-serine: 161 mg (0.21 mmol) of 1-O-hexadecyl-2-chloro-2-deoxyglycero-3-phospho-N-tert-butoxycarbonyl-L-serine benzhydryl ester is dissolved in 30 ml of dry chloroform and dry HCl gas is passed through for 15 minutes with stirring at 0° C. Dry nitrogen is then introduced for 1 hour. The solution is then washed with dilute aqueous ammonia and water and evaporated.

The crude product thus obtained is purified through silica gel (10 g SG 60, Merck 40–63 μm; eluting agent: CHCl3/CH3OH, 2:1 v/v with an increasing methanol gradient). After fractions, which are uniform in the thin-layer chromatogram, are combined and the solvent is evaporated, 38 mg (36% of theoretical) of pure product is obtained.

Rf: 0.13 (silica gel 60, Merck aluminum sheet; CHCl3/CH3OH/H2O=50:25:4, v/v/v).

C22H45ClPNO7 (502.02) calc. C 52.63, H 9.04, N 2.79, found C 51.76, H 8.82, N 2.60.

The preparation in Examples 2–9 proceeds analogously to the instructions given in Example 1:

EXAMPLE 2:

1-O-Hexadecyl-2-fluoro-1-deoxyglycero-3-phospho-L-serine

1-O-Hexadecyl-2-fluoro-2-deoxyglycero-3-phosphoric acid: from 334 mg (1.05 mmol) of 1-O-hexadecyl-2-fluoro-2-deoxyglycerol. Yield: 320 mg (76% of theoretical).

Rf: 0.15 (silica gel 60, Merck aluminum sheet; CHCl3/CH3OH/25% NH3=50:25:6, v/v/v).

1-O-Hexadecyl-2-fluoro-2-deoxyglycero-3-phospho-N-tert-butoxycarbonyl-L-serine benzhydryl ester: from 184 mg (0.46 mmol) of 1-O-hexadecyl-2-fluoro-2- deoxyglycero-3-phosphoric acid. Yield: 190 mg (54% of theoretical) of pure product.

Rf: 0.75 (silica gel 60, Merck aluminum sheet; CHCl3/CH3OH/25% NH3=65:35:5, v/v/v).

1-O-Hexadecyl-2-fluoro-2-deoxyglycero-3-phospho-L-serine: from 190 mg (0.25 mmol) of 1-O-hexadecyl-2-fluoro-2-deoxyglycero-3-phospho-N-tert-butoxycarbonyl-L-serine benzhydryl ester. Yield: 88 mg (72% of theoretical) of pure product.

Rf: 0.12 (silica gel 60, Merck aluminum sheet; CHCl3/CH3OH/H2O=50:25:4, v/v/v).

EXAMPLE 3

1-Chloro-1-deoxy-3-O-hexadecylglycero-2-phospho-L-serine

1-Chloro-1-deoxy-3-O-hexadecylglycero-2-phosphoric acid: from 350 mg (1.05 mmol) of 1-chloro-1-deoxy-3-O-hexadecylglycerol. Yield: 322 mg (74% of theoretical).

Rf: 0.18 (silica gel 60, Merck aluminum sheet; CHCl3/CH3OH/25% NH3=50:25:6, v/v/v).

1-Chloro-1-deoxy-3-O-hexadecylglycero-2-phospho-N-tert-butoxycarbonyl-L-serine benzhydryl ester: from 322 mg (0.77 mmol) of 1-chloro-1-deoxy-3-O-hexadecyl- glycero-2-phosphoric acid. Yield: 318 mg (53% of theoretical) of pure product.

Rf: 0.80 (silica gel 60, Merck aluminum sheet; CHCl3/CH3OH/25% NH3=65:35:5, v/v/v).

1-Chloro-1-deoxy-3-O-hexadecylglycero-2-phospho-L-serine: from 308 mg (0.40 mmol) of 1-chloro-1-deoxy-3-O-hexadecyl- glycero-2-phospho-N-tert-butoxycarbonyl-L-serine benzhydryl ester. Yield: 87 mg (43% of theoretical) of pure product.

Rf: 0.13 (silica gel 60, Merck aluminum sheet; CHCl3/CH3OH/H2O=50:25:4, v/v/v).

EXAMPLE 4

1-Chloro-1-deoxy-3-O-octadecylglycero-2-phospho-L-serine

1-Chloro-1-deoxy-3-O-octadecylglycero-2-phosphoric acid: from 417 mg (1.15 mmol) of 1-chloro-1-deoxy-3-O-octadecylglycerol. Yield: 450 mg (89% of theoretical).

Rf: 0.18 (silica gel 60, Merck aluminum sheet; CHCl3/CH3OH/25% NH3=50:25:6, v/v/v).

1-Chloro-1-deoxy-3-O-octadecylglycero-2-phospho-N-tert-butoxycarbonyl-L-serine benzhydryl ester: from 320 mg (0.72 mmol) of 1-chloro-1-deoxy-3-O-octadecylglycero-2-phosphoric acid. Yield: 258 mg (45% of theoretical) of pure product.

Rf: 0.80 (silica gel 60, Merck aluminum sheet; CHCl3/CH3OH/25% NH3=65:35:5, v/v/v).

1-Chloro-1-deoxy-3-O-octadecylglycero-2-phospho-L-serine: from 258 mg (0.32 mmol) of 1-chloro-1-deoxy-3-O-octadecyl- glycero-2-phospho-N-tert-butoxycarbonyl-L-serine benzhydryl ester. Yield: 61 mg (36% of theoretical) of pure product.

Rf: 0.13 (silica gel 60, Merck aluminum sheet; CHCl3/CH3OH/H2O=50:25:4, v/v/v).

EXAMPLE 5

1-O-Octadecyl-2-fluoro-2-deoxyglycero-3-phospho-L-serine

1-O-Octadecyl-2-fluoro-deoxyglycero-3-phosphoric acid: from 346 mg (1 mmol) of 1-O-octadecyl-2-fluoro-2-deoxyglycerol. Yield: 324 mg (76% of theoretical).

Rf: 0.15 (silica gel 60, Merck aluminum sheet; CHCl3/CH3OH/25% NH3=50:25:6, v/v/v).

1-O-Octadecyl-2-fluoro-2-deoxyglycero-3-phospho-N-tert-butoxycarbonyl-L-serine benzhydryl ester: from 307 mg (0.72 mmol) of 1-O-octadecyl-2-fluoro-2-deoxyglycero-3-phosphoric acid. Yield: 281 mg (50% of theoretical) of pure product.

Rf: 0.75 (silica gel 60, Merck aluminum sheet; CHCl3/CH3OH/25% NH3=65:35:5, v/v/v).

1-O-Octadecyl-2-fluoro-2-deoxyglycero-3-phospho-L-serine: from 281 mg (0.36 mmol) of 1-O-ocadecyl-2-fluoro-2-deoxy- glycero-3-phospho-N-tert-butoxycarbonyl-L-serine benzhydryl ester. Yield: 54 mg (29% of theoretical) of pure product.

Rf: 0.13 (silica gel 60, Merck aluminum sheet; CHCl3/CH3OH/H2O=50:25:4, v/v/v).

EXAMPLE 6

1-O-Octadecyl-2-chloro-2-deoxyglycero-3-phospho-L-serine

1-O-Octadecyl-2-chloro-2-deoxyglycero-3-phosphoric acid: from 544 mg (1.5 mmol) of 1-O-octadecyl-2-chloro-2-deoxyglycerol. Yield: 597 mg (90% of theoretical).

Rf: 0.16 (silica gel 60, Merck aluminum sheet; CHCl3/CH3OH/25% NH3=50:25:6, v/v/v).

1-O-Octadecyl-2-chloro-2-deoxyglycero-3-phospho-N-tert-butoxycarbonyl-L-serine benzhydryl ester: from 443 mg (1 mmol) of 1-O-octadecyl-2-chloro-2-deoxyglycero-3-phosphoric acid. Yield: 382 mg (48% of theoretical) of pure product.

Rf: 0.80 (silica gel 60, Merck aluminum sheet; CHCl3/CH3OH/25% NH3=65:35:5, v/v/v).

1-O-Octadecyl-2-chloro-2-deoxyglycero-3-phospho-L-serine: from 382 mg (0.48 mmol) of 1-O-octadecyl-2- chloro-2-deoxyglycero-3-phospho-N-tert-butoxycarbonyl-L-serine benzhydryl ester. Yield: 102 mg (40% of theoretical) of pure product.

Rf: 0.13 (silica gel 60, Merck aluminum sheet; CHCl3/CH3OH/H2O=50:25:4, v/v/v).

EXAMPLE 7

1-O-Tetradecyl-2-chloro-2-deoxyglycero-3-phospho-L-serine

1-O-Tetradecyl-2-chloro-2-deoxyglycero-3-phosphoric acid: from 368 mg (1.2 mmol) of 1-O-tetradecyl-2-chloro-2-deoxyglycerol. Yield: 445 mg (96% of theoretical).

Rf: 0.14 (silica gel 60, Merck aluminum sheet; CHCl3/CH3OH/25% NH3=50:25:6, v/v/v).

1-O-Tetradecyl-2-chloro-2-deoxyglycero-3-phospho-N-tert-butoxycarbonyl-L-serine benzhydryl ester: from 425 mg (1.1 mmol) of 1-O-tetradecyl-2-chloro-2-deoxyglycero-3-phosphoric acid. Yield: 423 mg (52% of theoretical) of pure product.

Rf: 0.72 (silica gel 60, Merck aluminum sheet; CHCl3/CH3OH/25% NH3=65:35:5, v/v/v).

1-O-Tetradecyl-2-chloro-2-deoxyglycero-3-phospho-L-serine: from 192 mg (0.26 mmol) of 1-O-tetradecyl-2-chloro-2-deoxyglycero-3-phospho-N-tert-butoxycarbonyl-L-serine benzhydryl ester. Yield: 39.5 mg (32% of theoretical) of pure product.

Rf: 0.13 (silica gel 60, Merck aluminum sheet; CHCl3/CH3OH/H2O=50:25:4, v/v/v).

EXAMPLE 8

1-O-(1-Methylheptadecyl)-2-chloro-2-deoxyglycero-3-phospho-L-serine

1-O-(1-Methylheptadecyl)-2-chloro-2-deoxyglycero-3-phosphoric acid: from 363 mg (1 mmol) of 1-O-(1-Methylheptadecyl)-2-chloro-2-deoxyglycerol. Yield: 372 mg (84% of theoretical).

Rf: 0.15 (silica gel 60, Merck aluminum sheet; CHCl3/CH3OH/25% NH3=50:25:6, v/v/v).

1-O-(1-Methylheptadecyl)-2-chloro-2-deoxyglycero-3-phospho-N-tert-butoxycarbonyl-L-serine benzhydryl ester: from 350 mg (0.79 mmol) of 1-O-(1-methylheptdeycl)-2-chloro-2-deoxyglycero-3-phosphoric acid. Yield: 371 mg (59% of theoretical) of pure product.

Rf: 0.80 (silica gel 60, Merck aluminum sheet; CHCl3/CH3OH/25% NH3=65:35:5, v/v/v).

1-O-(1-Methylheptadecyl)-2-chloro-2-deoxyglycero-3-phospho-L-serine: from 370 mg (0.59 mmol) of 1-O-(1-methylheptadecyl)-2-chloro-2-deoxyglycero-3-phospho-N-tert-butoxycarbonyl-L-serine benzhydryl ester. Yield: 122 mg (39% of theoretical) of pure product.

Rf: 0.14 (silica gel 60, Merck aluminum sheet; CHCl3/CH3OH/H2O=50:25:4, v/v/v).

EXAMPLE 9

1-O-Pentyl-2-chloro-2-deoxyglycero-3-phospho-L-serine

1-O-Pentyl-2-chloro-2-deoxyglycero-3-phosphoric acid: from 271 mg (1.5 mmol) of 1-O-pentyl-2-chloro-2-deoxyglycerol. Yield: 250 mg (64% of theoretical).

Rf: 0.10 (silica gel 60, Merck aluminum sheet; CHCl3/CH3OH/25% NH3=50:25:6, v/v/v).

1-O-Pentyl-2-chloro-2-deoxyglycero-3-phospho-N-tert-butoxycarbonyl-L-serine benzhydryl ester: from 208 mg (0.8 mmol) of 1-O-pentyl-2-chloro-2-deoxyglycero-3-phosphoric acid. Yield: 407 mg (83% of theoretical) of pure product.

Rf: 0.70 (silica gel 60, Merck aluminum sheet; CHCl3/CH3OH/25% NH3=65:35:5, v/v/v).

1-O-Pentyl-2-chloro-2-deoxyglycero-3-phospho-L-serine: from 406 mg (0.66 mmol) of 1-O-pentyl-2-chloro-2-deoxyglycero-3-phospho-N-tert-butoxycarbonyl-L-serine benzhydryl ester. Yield: 64 mg (28% of theoretical) of pure product.

Rf: 0.11 (silica gel 60, Merck aluminum sheet; CHCl3/CH3OH/H2O=50:25:4, v/v/v).

EXAMPLE 10

1-O-Hexadecyl-2-deoxyglycero-3-phospho-L-serine

A mixture of 1 g of L-serine, 1.9 ml of 0.1M acetate buffer (pH 5.6) with 0.1M CaCl2, 40 mg of 1-O-hexadecyl-2-deoxyglycerophosphoric acid ethyl ester, 2 ml of ether/chloroform (9:1, v/v), and 100 mg of a phospholipase D preparation derived from approximately 500 g of white cabbage is vigorously stirred for 40 hours at 40° C.

After cooling to room temperature, 4.35 ml of 0.1M ethylenediaminetetracetic acid is added. The organic solvents are removed by introduction of nitrogen. The mixture is stirred for 30 minutes with the 4.3-fold volume of chloroform/methanol (5:8, v/v), and the separating unconverted serine is removed by suction.

The filtrate is stirred with 1 volume of water and 3.7 volumes of chloroform for 10 minutes; the organic phase is separated and evaporated. The resulting residue is separated in 20 g of carboxymethylcellulose (Servacel CM 52) by column chromatography, whereby elution proceeds sequentially with 75 ml of chloroform (fraction 1), 500 ml each of chloroform/methanol (9:1, 8:2, 7:3, 1:1, v/v) (fractions 2-5). The end product is obtained in pure form from fraction 5. Yield: 15 mg (33% of theoretical) of pure product.

Rf: 0.13 (Merck, silica gel 60, precoated plate; CHCl3/CH3OH/H2O=50:25:4, v/v/v).

The preparation in Examples 11-21 proceeds analogously to these instructions.

EXAMPLE 11

1-O-Hexadecyl-2-O-(2,2,2-trifluoroethyl)-glycero-3-phospho-L-serine from 40 mg of 1-O-hexadecyl-2-O-(2,2,2-trifluoroethyl)-glycero-3-phosphocholine. Yield: 12 mg (30% of theoretical) of pure product.

Rf: 0.13 (Merck silica gel 60, precoated plate; CHCl3/CH3OH/H2O=50:25:4, v/v/v).

EXAMPLE 12

1-O-Hexadecyl-2-O-(2,2,2-trifluoroethyl)-glycero-3-phospho-L-serine from 40 mg of 1-O-hexadecyl-2-O-(2,2,2-trifluoroethyl)glycero-3-phosphoric acid-2-bromoethyl ester) Yield: 13.5 mg (35% of theoretical) of pure product.

Rf: 0.13 (Merck silica gel 60, precoated plate; CHCl3/CH3OH/H2O=50:25:4, v/v/v).

EXAMPLE 13

1-Chloro-1-deoxy-2-O-hexadecylglycero-3-phospho-L-serine from 40 mg of 1-chloro-1-deoxy-2-O-hexadecylglycero-3-phosphocholine Yield: 15 mg (37% of theoretical) of pure product.

Rf: 0.14 (Merck silica gel 60, precoated plate; CHCl3/CH3OH/H2O=50:25:4, v/v/v).

EXAMPLE 14

1-O-(2,2,2-trifluoroethyl)-2-O-hexadecylglycero-3-phospho-L-serine from 40 mg of 1-O-(2,2,2-trifluoroethyl)-2-O-hexadecylglycero-3-phosphocholine. Yield: 18 mg (44% of theoretical) of pure product.

Rf: 0.13 (Merck silica gel 60, precoated plate; CHCl3/CH3OH/H2O=50:25:4, v/v/v).

EXAMPLE 15

1-O-Eicosanyl-2-chloro-2-deoxyglycero-3-phospho-L-serine from 40 mg of 1-O-eicosanyl-2-chloro-2-deoxyglycero-3-phosphoric acid-n-butyl ester. Yield: 14.5 mg (34% of theoretical) of pure product.

Rf: 0.15 (Merck silica gel 60, precoated plate; CHCl3/CH3OH/H2O=50:25:4, v/v/v).

EXAMPLE 16

1-O-Triacontyl-2-chloro-2-deoxyglycero-3-phospho-L-serine from 60 mg of 1-O-triacontyl-2-chloro-2-deoxyglycero-3-phosphoric acid ethyl ester. Yield: 14 mg (33% of theoretical) of pure product.

Rf: 0.20 (Merck silica gel 60, precoated plate; CHCl3/CH3OH/H2O=50:25:4, v/v/v).

EXAMPLE 17

1-O-Octadecyl-2-O-(2,2,2-trifluoroethyl)-glycero-3-phospho-L-serine from 40 mg of 1-O-octadecyl-(2,2,2-trifluoroethyl)-glycero-3-phosphoric acid-2-bromoethyl ester. Yield: 13.5 mg (32% of theoretical) of pure product.

Rf: 0.14 (Merck silica gel 60, precoated plate; CHCl3/CH3OH/H2O=50:25:4, v/v/v).

EXAMPLE 18

1,2-Di-O-hexadecylglycero-3-phospho-L-serine from 40 mg of 1,2-di-O-hexadecylglycero-3-phosphocholine. Yield: 13 mg (32% of theoretical) of pure product.

Rf: 0.22 (Merck silica gel 60, precoated plate; CHCl3/CH3OH/H2O=50:25:4, v/v/v).

EXAMPLE 19

1-O-Eicosanyl-2-O-(2,2,2-trifluoroethyl)-glycero-3-phospho-L-serine from 40 mg of 1-O-eicosanyl-2-O-(2,2,2-trifluoroethyl)glycero-3-phosphocholine. Yield: 16 mg (40% of theoretical) of pure product.

Rf: 0.14 (Merck silica gel 60, precoated plate; CHCl3/CH3OH/H2O=50:25:4, v/v/v).

EXAMPLE 20

1-Chloro-1-deoxy-3-O-(cis-9-octadecenyl)-glycero-2-phospho-L-serine from 40 mg of 1-chloro-1-deoxy-3-O-(cis-9-octadecenyl)-glycero-2-phosphoric acid ethyl ester. Yield: 15.5 mg (34% of theoretical) of pure product.

Rf: 0.13 (Merck silica gel 60, precoated plate; CHCl3/CH3OH/H2O=50:25:4, v/v/v).

EXAMPLE 21

1-O-(2-Methoxyoctadecyl)-2-chloro-2-deoxyglycero-3-phospho-L-serin from 50 mg of 1-O-(2-methoxyoctadecyl)-2-chloro-2-deoxyglycero-3-phosphoric acid ethyl ester. Yield: 16 mg (28% of theoretical) of pure product.

Rf: 0.15 (Merck silica gel 60, precoated plate; CHCl3/CH3OH/H2O=50:25:4, v/v/v).

We claim:

1. A glycero-3(2)-phospho-L-serine compound selected from the group consisting of: 1-O-hexadecyl-2-chloro-2-deoxyglycero-3-phospho-L-serine, 1-O-hexadecyl-2-fluoro-2-deoxyglycero-3-phospho-L-serine, 1-chloro-1-deoxy-3-O-hexadecylglycero-2-phospho-L-serine, and 1-O-(2,2,2-trifluoroethyl)-2-O-hexadecylglycero-3-phospho-L-serine.

* * * * *